US011249299B2

(12) United States Patent
Hanzawa et al.

(10) Patent No.: US 11,249,299 B2
(45) Date of Patent: Feb. 15, 2022

(54) STEREOSCOPIC VISION OPTICAL SYSTEM AND ENDOSCOPE USING THE SAME

(71) Applicant: OLYMPUS CORPORATION, Hachioji (JP)

(72) Inventors: Toyoharu Hanzawa, Mitaka (JP); Takeshi Suga, Hino (JP)

(73) Assignee: OLYMPUS CORPORATION, Tokyo (JP)

( * ) Notice: Subject to any disclaimer, the term of this patent is extended or adjusted under 35 U.S.C. 154(b) by 57 days.

(21) Appl. No.: 16/800,962

(22) Filed: Feb. 25, 2020

(65) Prior Publication Data

US 2020/0192077 A1    Jun. 18, 2020

Related U.S. Application Data

(63) Continuation of application No. PCT/JP2018/031718, filed on Aug. 28, 2018.

(30) Foreign Application Priority Data

Nov. 30, 2017    (JP) .............................. JP2017-230007

(51) Int. Cl.
*G02B 23/24*    (2006.01)
*A61B 1/00*    (2006.01)
(Continued)

(52) U.S. Cl.
CPC ...... *G02B 23/2415* (2013.01); *A61B 1/00188* (2013.01); *A61B 1/00193* (2013.01);
(Continued)

(58) Field of Classification Search
CPC ............ G02B 23/2415; A61B 1/00163; A61B 1/00193
(Continued)

(56) References Cited

U.S. PATENT DOCUMENTS 10,105,034 B2    10/2018  Suga
10,274,717 B2    4/2019   Togino
(Continued)

FOREIGN PATENT DOCUMENTS

JP    2014160240 A    9/2014
JP    2014174390 A    9/2014
(Continued)

OTHER PUBLICATIONS

International Search Report (ISR) dated Dec. 4, 2018 (and English translation thereof) issued in International Application No. PCT/JP2018/031718.
(Continued)

*Primary Examiner* — Darryl J Collins
(74) *Attorney, Agent, or Firm* — Holtz, Holtz & Volek PC

(57) ABSTRACT

A stereoscopic vision optical system includes a first lens group having a negative refractive power, disposed nearest to an object, a second lens group having a positive refractive power, and a rear-side lens group having a positive refractive power. The rear-side lens group includes a first rear group and a second rear group. The optical axis of the first lens group, an optical axis of the first rear group, and an optical axis of the second rear group is positioned on the same plane. The optical axis of the first lens group is positioned between the optical axis of the first rear group and the optical axis of the second rear group, and the following conditional expression (1) is satisfied:

$$0.08 \leq ((-L/2) \times (f1/f2)) \times (1/WD) \leq 0.25 \qquad (1).$$

9 Claims, 10 Drawing Sheets

(51) Int. Cl.
*G02B 15/14* (2006.01)
*G03B 35/08* (2021.01)
*G02B 9/04* (2006.01)

(52) U.S. Cl.
CPC ......... *G02B 15/1425* (2019.08); *G03B 35/08* (2013.01); *G02B 9/04* (2013.01)

(58) Field of Classification Search
USPC ........................................................ 600/111
See application file for complete search history.

(56) References Cited

U.S. PATENT DOCUMENTS

| | | |
|---|---|---|
| 2016/0320606 A1 | 11/2016 | Togino |
| 2016/0338576 A1* | 11/2016 | Namii ................. A61B 1/00193 |
| 2017/0258297 A1 | 9/2017 | Suga |
| 2018/0095262 A1 | 4/2018 | Fukushima |
| 2018/0295265 A1 | 10/2018 | Suga |

FOREIGN PATENT DOCUMENTS

| | | |
|---|---|---|
| JP | 6072381 B1 | 1/2017 |
| JP | 6072392 B1 | 1/2017 |
| WO | 2017017854 A1 | 2/2017 |

OTHER PUBLICATIONS

Written Opinion of the International Searching Authority dated Dec. 4, 2018 issued in International Application No. PCT/JP2018/031718.

International Preliminary Report on Patentability (IPRP) (and English language translation thereof) dated Jun. 11, 2020 issued in International Application No. PCT/JP2018/031718.

Chinese Office Action (and English language translation thereof) dated Jun. 24, 2021 issued in counterpart Chinese Application No. 201880066053.X.

* cited by examiner

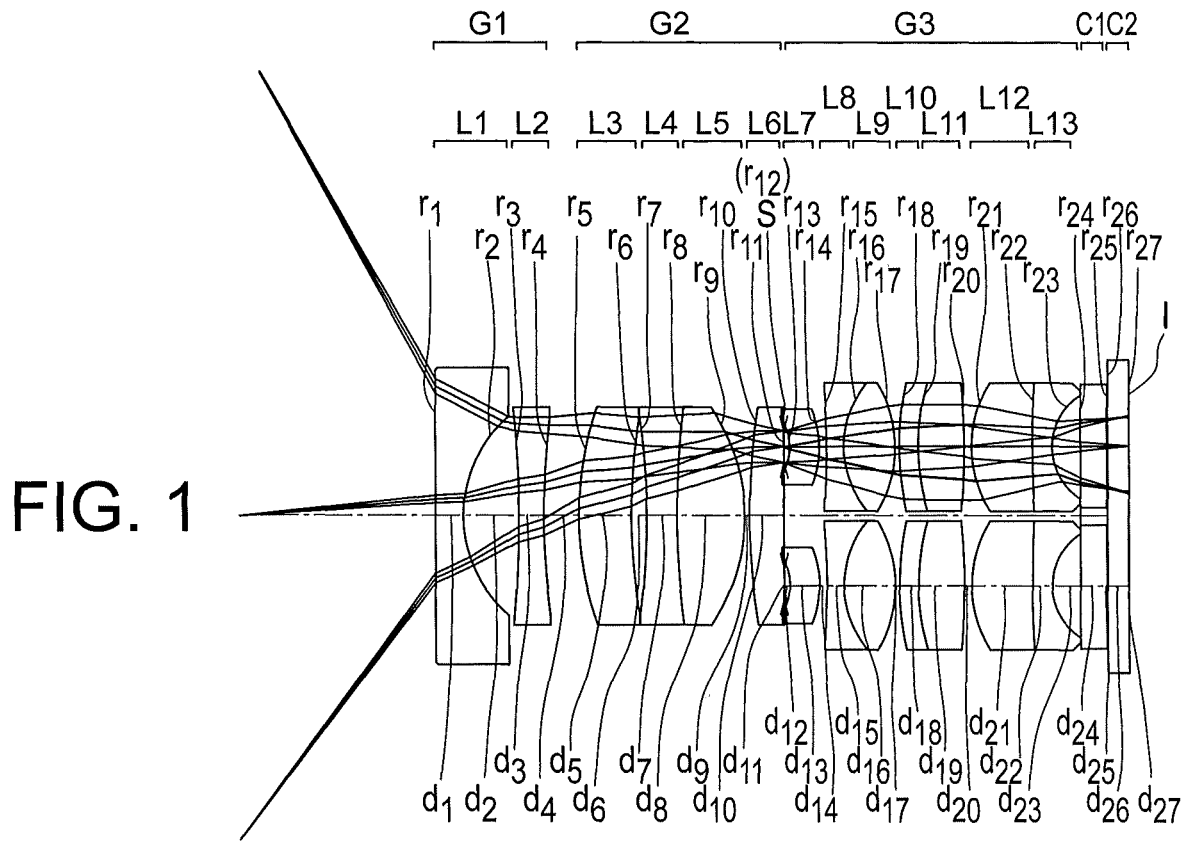
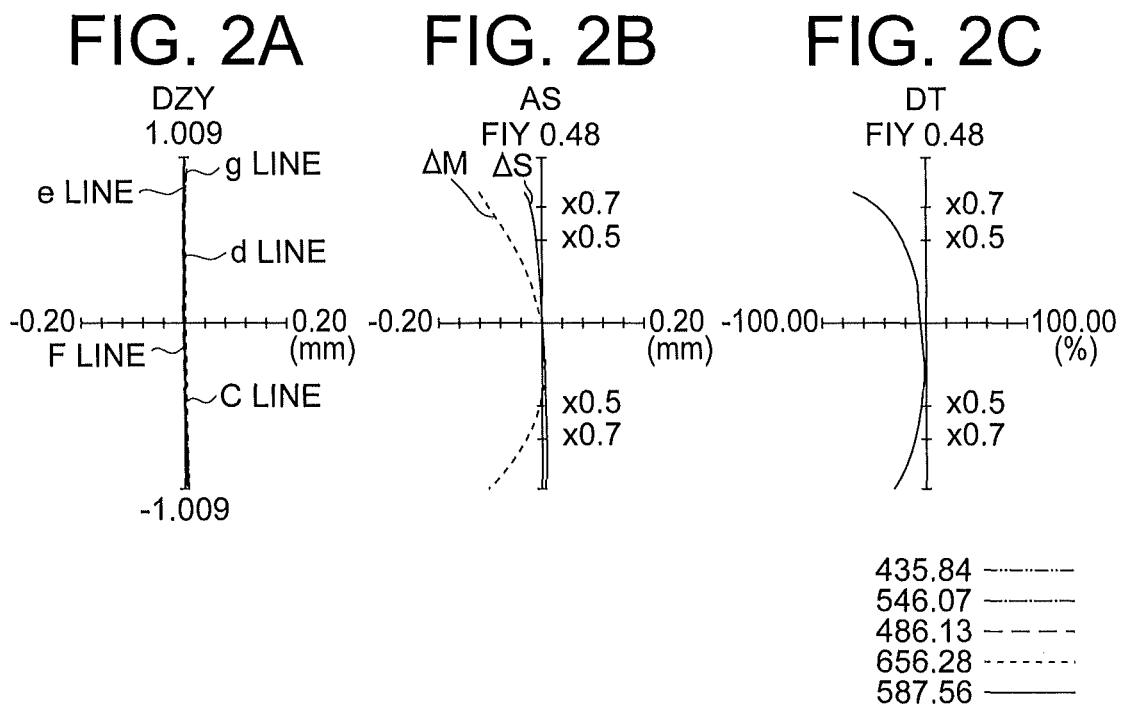

DZY
1.019

AS
FIY 0.48

DT
FIY 0.48

DZY
1.009

AS
FIY 0.48

DT
FIY 0.48

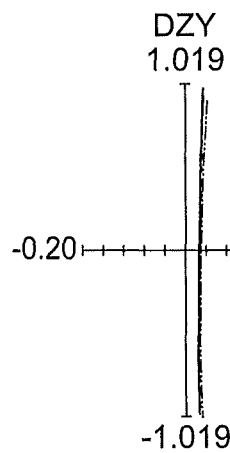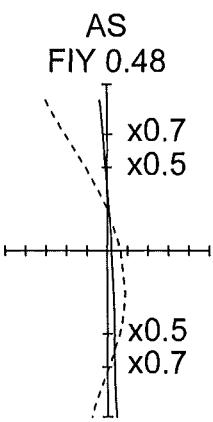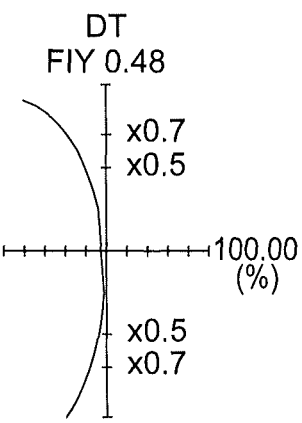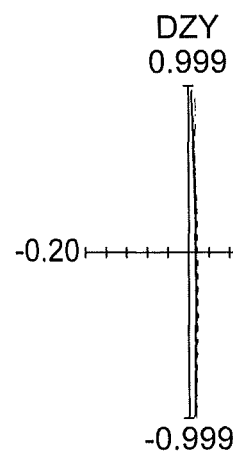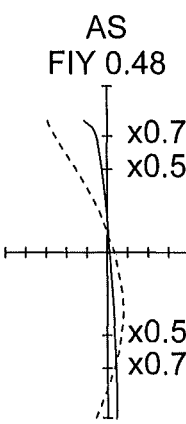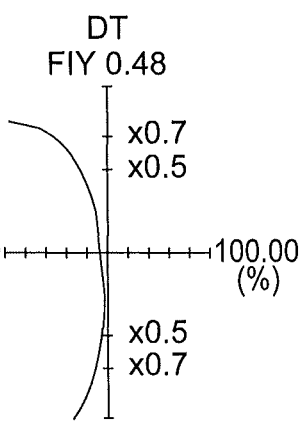

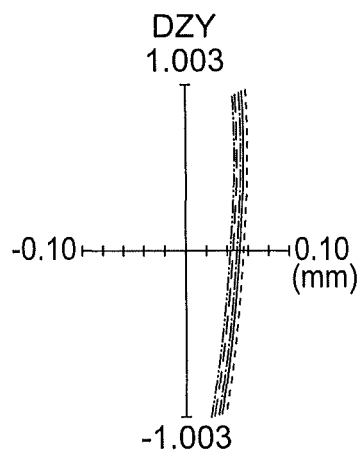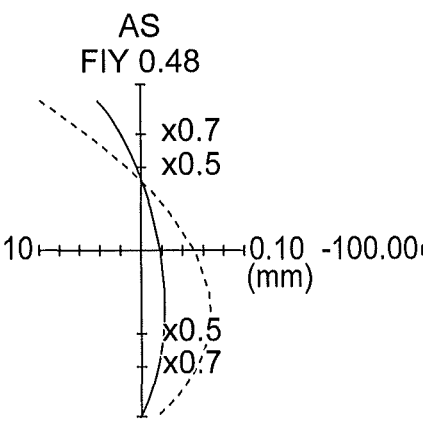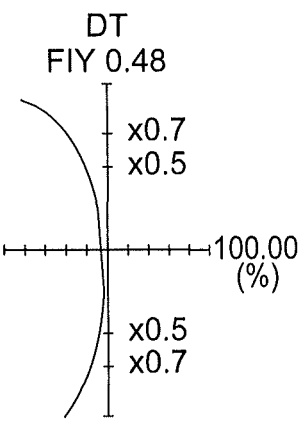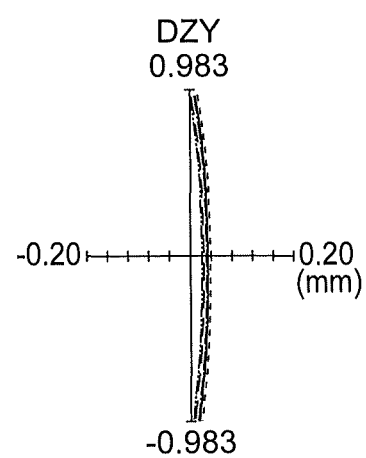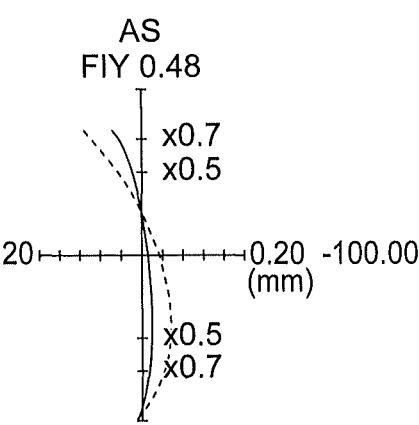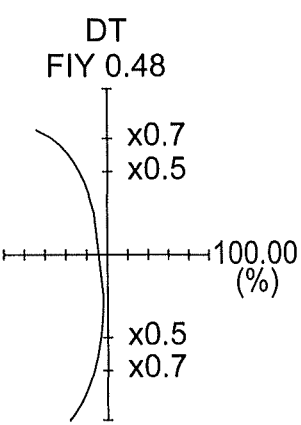

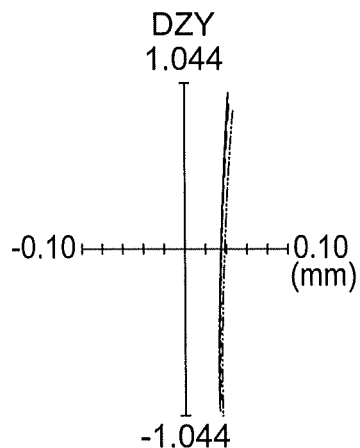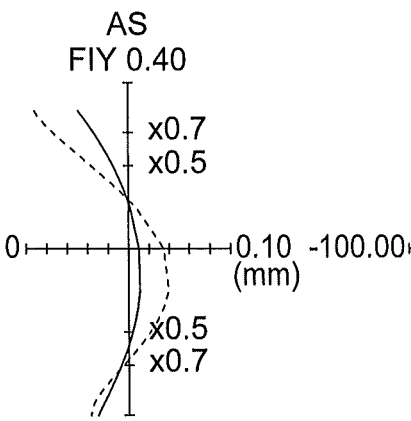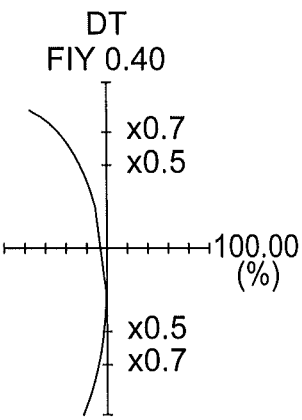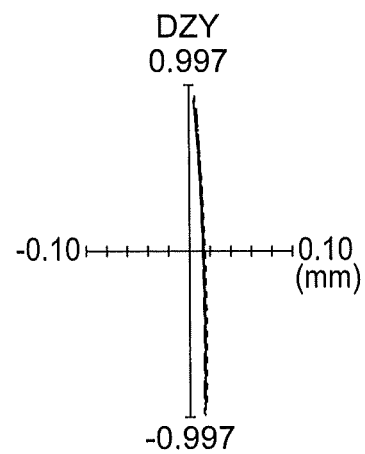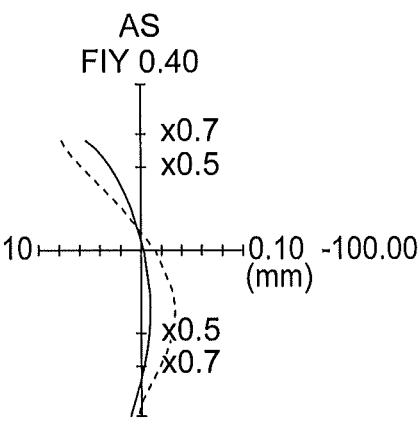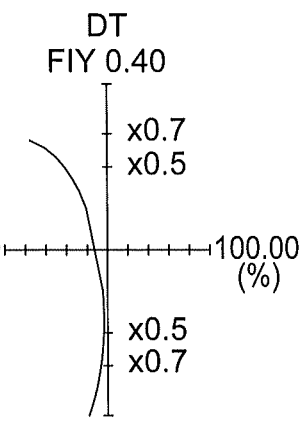

STEREOSCOPIC VISION OPTICAL SYSTEM AND ENDOSCOPE USING THE SAME

CROSS-REFERENCE TO RELATED APPLICATION

The present application is a continuation application of International Application No PCT/JP2018/031718 filed on Aug. 28, 2018 which is based upon and claims the benefit of priority from Japanese Patent Application No. 2017-230007 filed on Nov. 30, 2017; the entire contents of which are incorporated herein by reference.

BACKGROUND

Technical Field

The present disclosure relates a stereoscopic vision optical system, and an endoscope using the same.

Description of the Related Art

In diagnosis by an endoscope, magnified observation which enables to know a stereoscopic structure of a tissue in more detail has been considered effective. In an optical system carrying out the magnified observation, by moving a position of an object point in focus from a far point to a near point, it is possible to make a magnified display of the tissue.

Out of a range that enables to bring to focus (hereinafter, referred to as 'focus range'), a position of an object point farthest from the optical system is a far point, and a position of an object point nearest to the optical system is a near point. Moreover, a near-point observation is an observation in a state of being focused to an object at the near point and a far-point observation is an observation in a state of being focused to an object at a far point.

In an endoscope, at the time of the near-point observation, acquisition of stereoscopic information of an object is desired. It is possible to acquire the stereoscopic information by viewing stereoscopically. In stereoscopic vision, a pair of images having a parallax is used.

The pair of images having a parallax is captured from a pair of optical images having a parallax. It is possible to form the pair of optical images having a parallax by disposing a pair of optical systems in parallel. An optical system which forms the pair of optical images is disclosed in Japanese Patent No. 6072392 Publication and Japanese Patent No. 6072381 Publication.

In Japanese Patent No. 6072392 Publication, an optical system having an optical system for the right eye and an optical system for the left eye has been disclosed. The optical system for the right eye and the optical system for the left eye are disposed in parallel.

In Japanese Patent No. 6072381 Publication, an image forming optical system which includes a first negative lens group having a negative refractive power, a first positive lens group having a positive refractive power, and a second positive lens group having a positive refractive power has been disclosed. The first negative lens group and the first positive lens group are disposed along a common central axis, and the second positive lens group is disposed side-by-side in a direction of parallax, interposing the common central axis.

In a case in which a pair of optical systems is disposed in parallel, light emerged from the same object point is incident on one optical system and the other optical system. Each of light incident on the one optical system and light incident on the other optical system passes through an opening portion of a stop.

Light passing through each opening portion is light emerged from the same object point. Therefore, a light ray passing through a center of the opening portion of the one optical system and a light ray passing through a center of the opening portion of the other optical system intersect at a position of the same object point. An angle of intersection of the two light rays is called as an inward angle. Since the center of the opening portion coincides with an optical axis of the optical system, the inward angle is determined by a distance between optical axes of the pair of optical systems and a distance between an object point and the optical system.

As the inward angle varies, the stereoscopic vision (hereinafter, referred to as 'stereoscopic effect') varies. Therefore, in a case of carrying out stereoscopic vision, it is significant that the inward angle has been set such that an appropriate stereoscopic effect is achieved.

SUMMARY

A stereoscopic vision optical system according to at least some embodiments of the present disclosure includes in order from an object side to an image side:

a first lens group having a negative refractive power, disposed nearest to an object, a second lens group having a positive refractive power, and a rear-side lens group having a positive refractive power, wherein the rear-side lens group includes a first rear group and a second rear group, the first lens group and the second lens group are aligned in a straight line, an optical axis of the first lens group and an optical axis of the second lens group coincide with the straight line, the optical axis of the first lens group, an optical axis of the first rear group, and an optical axis of the second rear group are positioned on the same plane, the optical axis of the first lens group is positioned between the optical axis of the first rear group and the optical axis of the second rear group, and the following conditional expression (1) is satisfied:

$$0.08 \leq ((-L/2) \times (f1/f2)) \times (1/WD) \leq 0.25 \quad (1)$$

where,

L denotes a distance between the optical axis of the first rear group and the optical axis of the second rear group, WD denotes a distance between an object best position and a surface nearest to the object of the first lens group, f1 denotes a focal length of the first lens group, f2 denotes a focal length of the second lens group, and the object best position is an object position conjugate with the most focused position on an image plane.

Moreover, another stereoscopic vision optical system according to at least some embodiments of the present disclosure includes in order from an object side to an image side:

a first lens group having a negative refractive power, disposed nearest to an object, a second lens group having a positive refractive power, and a rear-side lens group having a positive refractive power, wherein the rear-side lens group includes a first rear group and a second rear group, the first lens group and the second lens group are disposed such that aligned in a straight line, an optical axis of the first lens group and an optical axis of the second lens group coincide with the straight line, the optical axis of the first lens group, an optical axis of the first rear group, and an optical axis of the second rear group are positioned on the same plane, the optical axis of the first lens group is positioned between the optical axis of the first rear group and the optical axis of the second rear group, the second lens group or the rear-side lens group includes a movable lens, focusing is carried out by moving the movable lens parallel to the optical axis of the first lens group, and both in a case of being focused to an object at a far point and in a case of being focused to an object at a near point, the following conditional expression (2) is satisfied:

$$0.025 \leq ((-L/2) \times (f1/f2)) \times (1/WD') \leq 0.25 \quad (2)$$

where,

L denotes a distance between the optical axis of the first rear group and the optical axis of the second rear group, WD' denotes a distance between an object best position and a surface nearest to the object of the first lens group, f1 denotes a focal length of the first lens group, f2 denotes a focal length of the second lens group, and the object best position is an object position conjugate with the most focused position on an image plane.

Moreover, an endoscope according to at least some embodiments of the present disclosure includes:

a stereoscopic vision optical system, and an image sensor which captures an optical image formed by the stereoscopic vision optical system.

BRIEF DESCRIPTION OF THE DRAWINGS

FIG. 1 is a lens cross-sectional view of a stereoscopic vision optical system of an example 1;

FIG. 2A, FIG. 2B, and FIG. 2C are aberration diagrams of the stereoscopic vision optical system of the example 1;

FIG. 6A, FIG. 6B, FIG. 6C, FIG. 6D, FIG. 6E, and FIG. 6F are aberration diagrams of the stereoscopic vision optical system of the example 3;

FIG. 8A, FIG. 8B, FIG. 8C, FIG. 8D, FIG. 8E, and FIG. 8F are aberration diagrams of the stereoscopic vision optical system of the example 4;

FIG. 10A, FIG. 10B, FIG. 10C, FIG. 10D, FIG. 10E, and FIG. 10F are aberration diagrams of the stereoscopic vision optical system of the example 5.

DETAILED DESCRIPTION

Figure 3A:
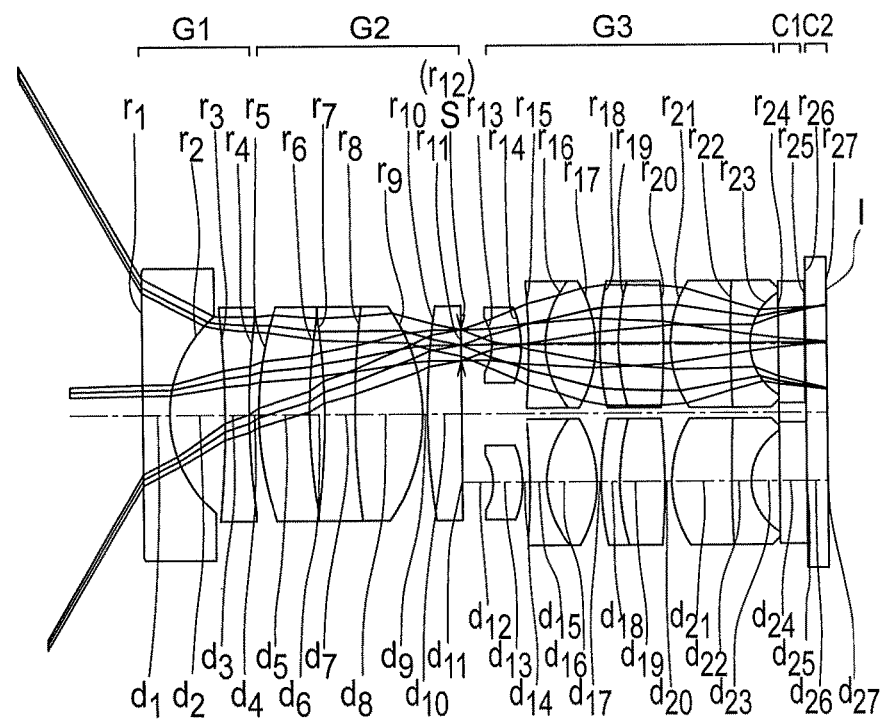
FIG. 3A and FIG. 3B are lens cross-sectional views of a stereoscopic vision optical system of an example 2.
Figure 3B:
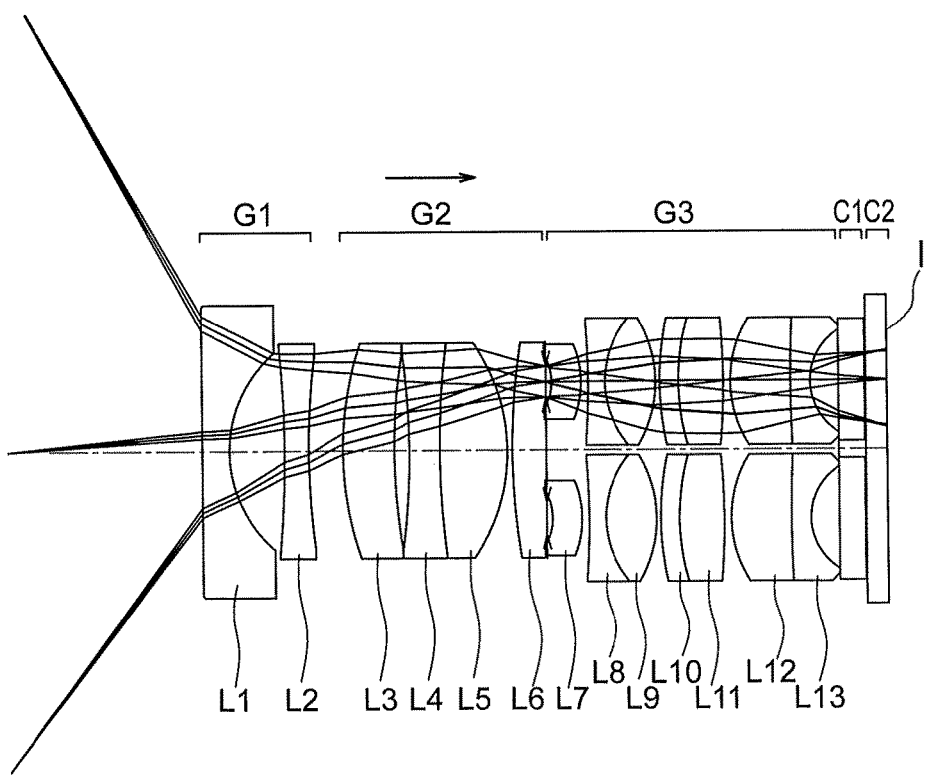
Figure 4A:
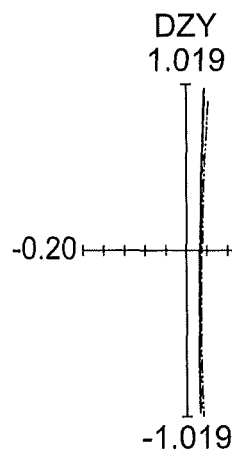
FIG. 4A, FIG. 4B, FIG. 4C, FIG. 4D, FIG. 4E, and FIG. 4F are aberration diagrams of the stereoscopic vision optical system of the example 2.
Figure 4B:
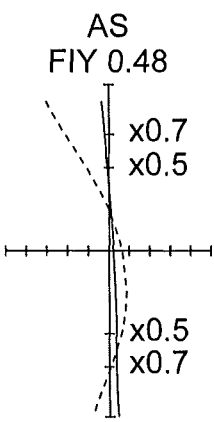
Figure 4C:
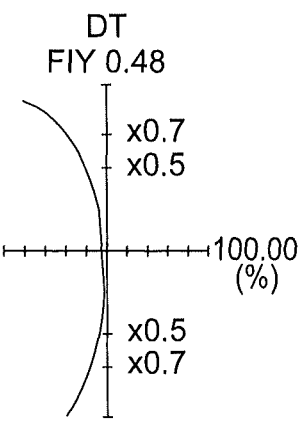
Figure 4D:
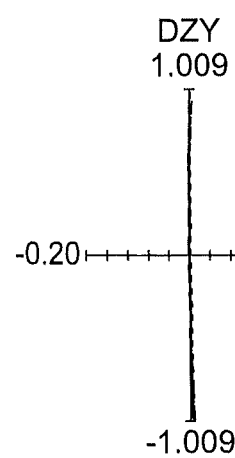
Figure 4E:
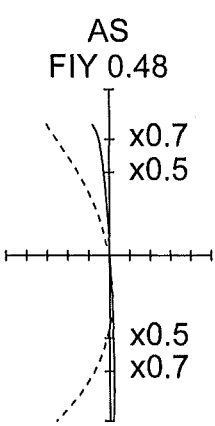
Figure 4F:
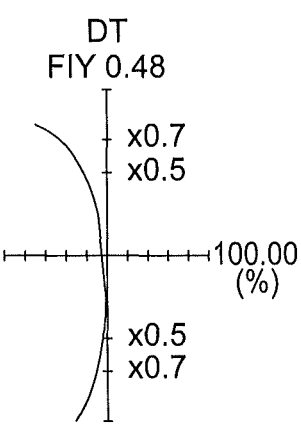
Figure 5A:
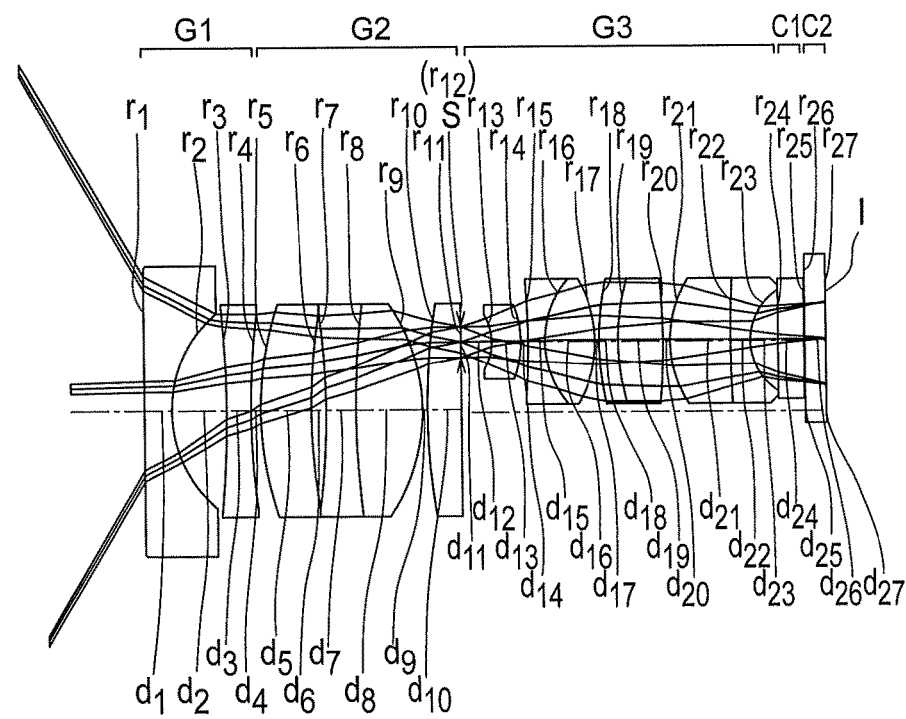
FIG. 5A and FIG. 5B are lens cross-sectional views of a stereoscopic vision optical system of an example 3.
Figure 5B:
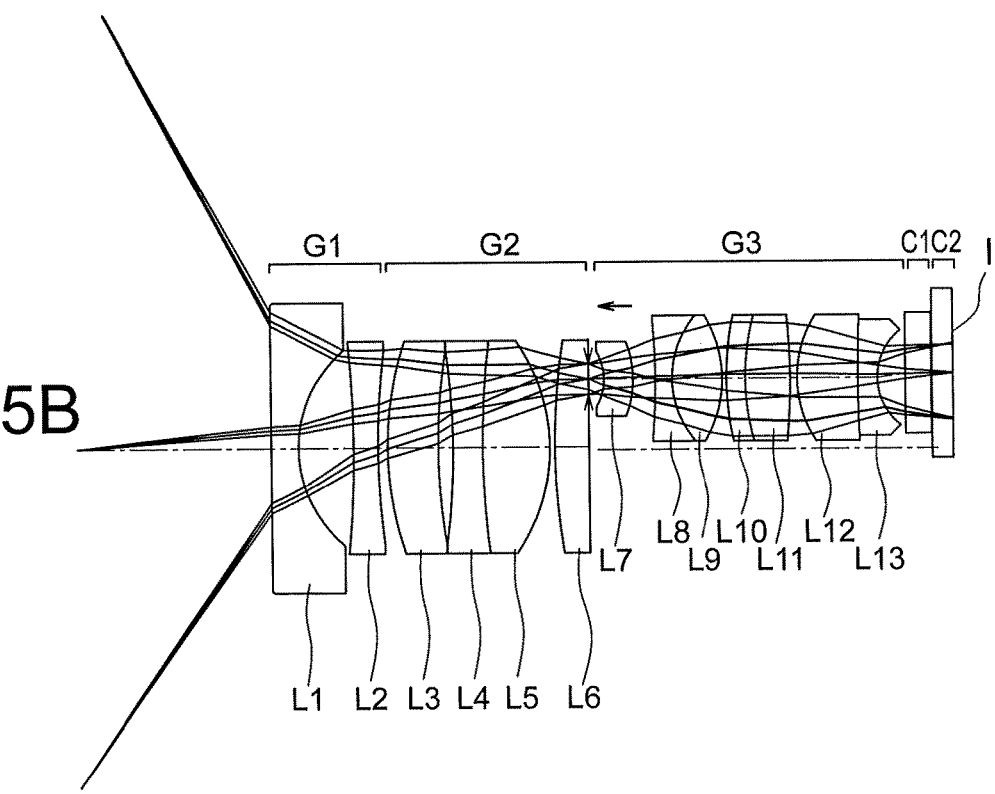
Figure 7A:
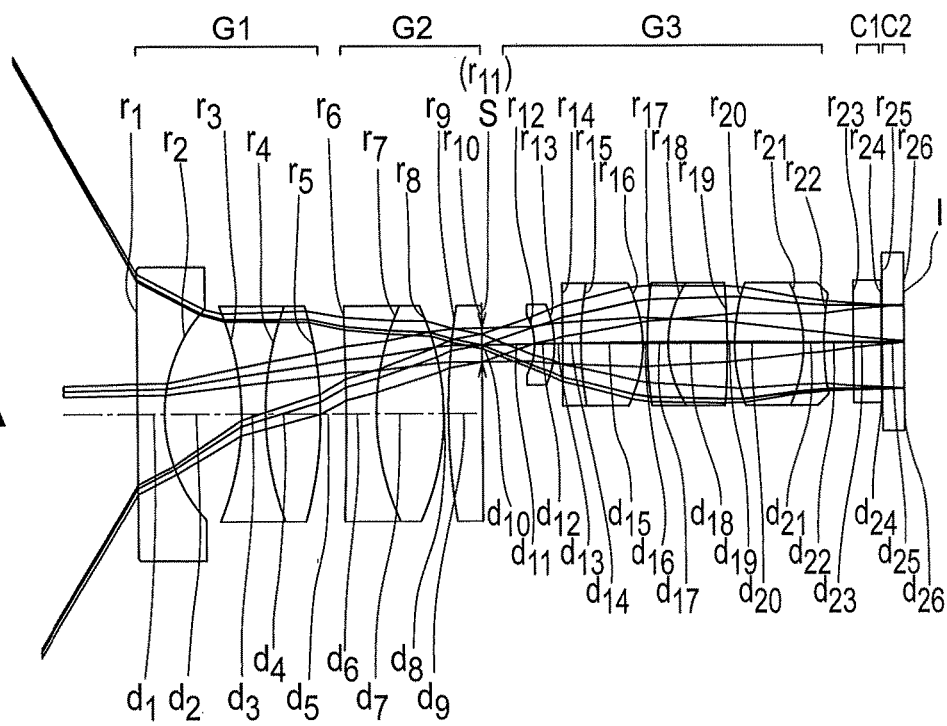
FIG. 7A and FIG. 7B are lens cross-sectional views of a stereoscopic vision optical system of an example 4.
Figure 7B:
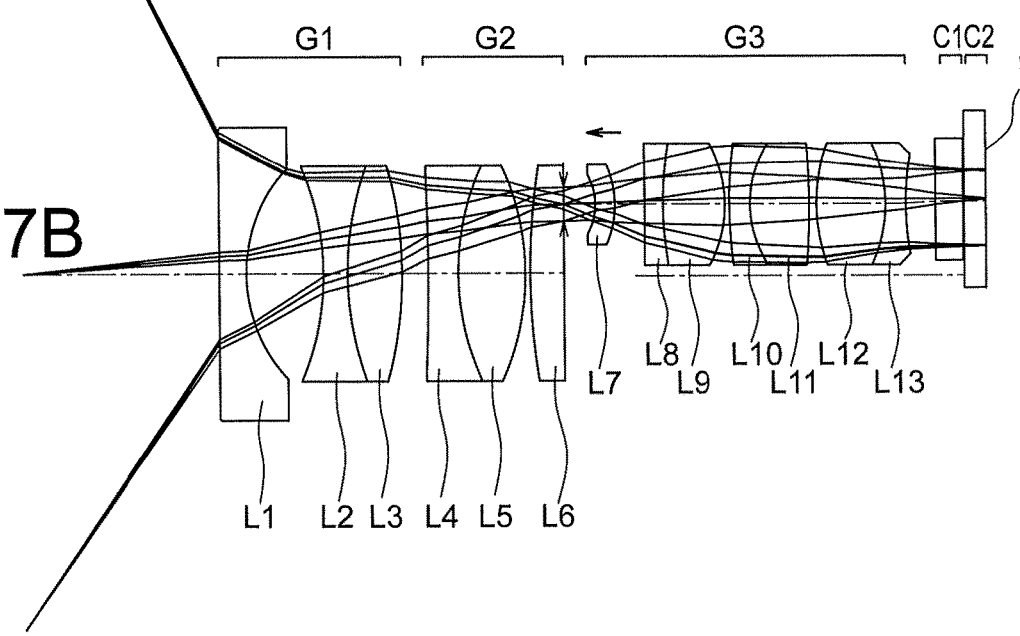
Figure 9A:
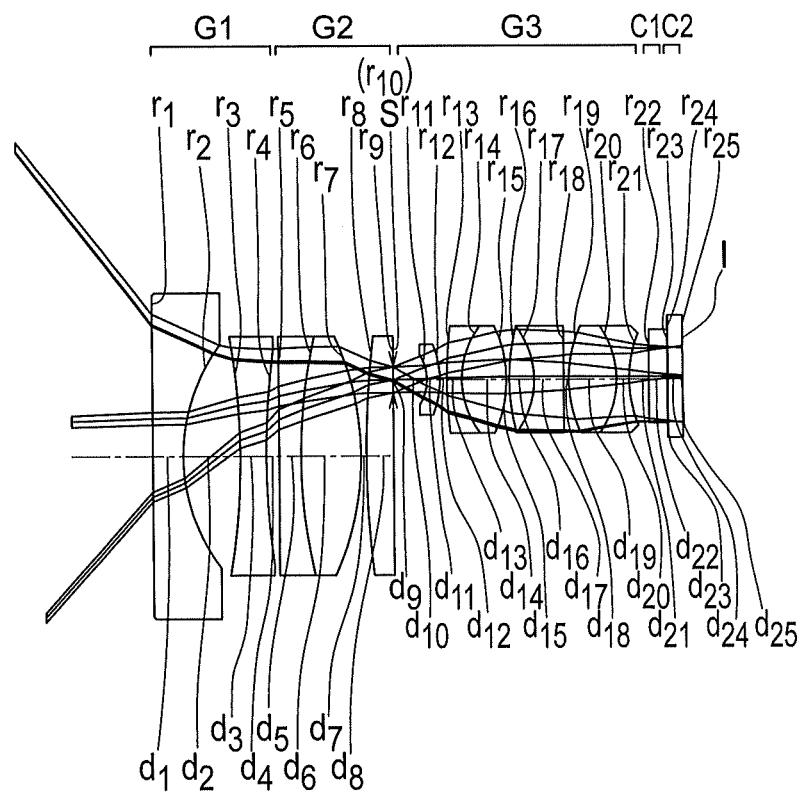
FIG. 9A and FIG. 9B are lens cross-sectional views of a stereoscopic vision optical system of an example 5.
Figure 9B:
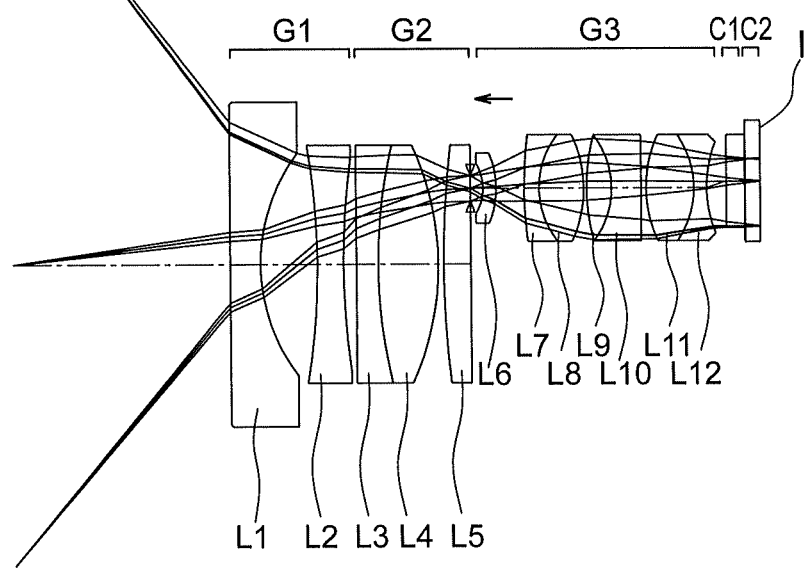

A stereoscopic vision optical system and an endoscope according to the present embodiments will be described below in detail by referring to the accompanying diagrams. However, the present disclosure is not restricted to the embodiments described below.

A stereoscopic vision optical system according to a first embodiment and a stereoscopic vision optical system according to a second embodiment has a basic arrangement (hereinafter, referred to as 'basic arrangement of the present embodiment'). Therefore, prior to describing the stereoscopic vision optical system according to the first embodiment and the stereoscopic vision optical system according to the second embodiment, the basic arrangement of the present embodiment will be described.

The basic arrangement of the present embodiment includes in order from an object side, a first lens group having a negative refractive power, a second lens group having a positive refractive power, and a rear-side lens group having a positive refractive power, and the rear-side lens group includes a first rear group and a second rear group, the first lens group and the second lens group are disposed such that an optical axis of the first lens group and an optical axis of the second lens group coincide, the optical axis of the first lens group, an optical axis of the first rear group, and an optical axis of the second rear group are positioned on the same plane, the optical axis of the first lens group is positioned between the optical axis of the first rear group and the optical axis of the second rear group.

As shown in Japanese Patent No. 6072392 Publication, in a stereoscopic vision optical system including only a pair of optical systems, no optical system other than the pair of optical systems has been disposed. Therefore, for making an inward angle small, a distance between the pair of optical systems has to be made narrow.

However, when the distance between the pair of optical systems is made narrow, the optical systems make a contact mutually. In such manner, in the stereoscopic vision optical system including only a pair of optical systems, there is a limitation on the inward angle that can be made small. Accordingly, it is not possible to make the inward angle in a state of the optical systems having made a contact mutually, smaller than an inward angle for which no fatigue occurs. Therefore, the fatigue occurs at the time of proximity observation.

In the basic arrangement of the present embodiment, the rear-side lens group includes the first rear group and the second rear group. Therefore, the basic arrangement of the present embodiment also has a pair of optical systems. However, the first lens group and the second lens group are disposed on the object side of the rear-side lens group.

The first lens group and the second lens group are disposed such that the optical axis of the first lens group and the optical axis of the second lens group coincide. Moreover, the optical axis of the first lens group is positioned between the optical axis of the first rear group and the optical axis of the second rear group. Therefore, the first lens group and the second lens group are optical systems common with respect to the pair of optical systems.

In such manner, in the basic arrangement of the present embodiment, a common optical system is provided apart from the pair of optical systems. In this case, it is possible to make a distance L between the pair of optical systems small optically by the common optical system. More specifically, the distance between the pair of optical systems becomes a value close to (f1/f2)×L. Here, f1 is a focal length of the first lens group and f2 is a focal length of the second lens group.

Therefore, in the basic arrangement of the present embodiment, it is possible to make the inward angle small without narrowing the distance between the first rear group and the second rear group. Accordingly, by making appropriate the distance between the pair of optical systems and disposing appropriately the refractive power of lenses of the common optical system, it is possible set the optimum inward angle.

The stereoscopic vision optical system according to the first embodiment has the abovementioned basic arrangement and the following conditional expression (1) is satisfied:

$$0.08 \leq ((-L/2) \times (f1/f2)) \times (1/WD) \leq 0.25 \quad (1)$$

where,

L denotes a distance between the optical axis of the first rear group and the optical axis of the second rear group, WD denotes a distance between an object best position and a surface nearest to an object of the first lens group, f1 denotes a focal length of the first lens group, f2 denotes a focal length of the second lens group, and the object best position is an object position conjugate with the most focused position on an image plane.

In a case of falling below a lower limit value of conditional expression (1), the inward angle becomes excessively small, even in a case in which the stereoscopic vision optical system includes the common optical system and the pair of optical systems. Consequently, it is not possible to achieve an adequate stereoscopic effect.

In a case of exceeding an upper limit value of conditional expression (1), the inward angle becomes excessively large. Consequently, when an attempt is made to carry out stereoscopic vision by using a pair of images, it becomes difficult to fuse the two images as a stereoscopic image. Moreover, when the stereoscopic vision is continued forcedly, eyestrain becomes substantial.

By satisfying conditional expression (1), it is possible to make the inward angle an appropriate angle. As a result, it is possible to achieve the adequate stereoscopic effect.

It is preferable that the following conditional expression (1') be satisfied instead of conditional expression (1).

$$0.1 \leq ((-L/2) \times (f1/f2)) \times (1/WD) \leq 0.22 \quad (1')$$

An optical image of an object is formed on the image plane. A relationship of the object best position and the optical image, for instance, is as follows. With a distance between a position of an object and the object best position becoming smaller, the optical image becomes sharper. Moreover, when the position of the object coincides with the object best position, the optical image becomes the sharpest. Therefore, the object best position can be said to be a position of an object when the sharpest optical image is formed.

The stereoscopic vision optical system according to the second embodiment has the abovementioned basic arrangement, and the second lens group or the rear-side lens group includes a movable lens, focusing is carried out by moving the movable lens along an optical axis, and both in a case of being focused to an object at a far point and in a case of being focused to an object at a near point, the following conditional expression (2) is satisfied:

$$0.025 \leq ((-L/2) \times (f1/f2)) \times (1/WD') \leq 0.25 \quad (2)$$

where,

L denotes a distance between the optical axis of the first rear group and the optical axis of the second rear group, WD' denotes a distance between an object best position and a surface nearest to an object of the first lens group, f1 denotes a focal length of the first lens group, f2 denotes a focal length of the second lens group, and the object best position is an object position conjugate with the most focused position on an image plane.

In the stereoscopic vision optical system according to the second embodiment, the second lens group or the rear-side lens group includes the movable lens, and focusing is carried out by moving the movable lens along the optical axis. Accordingly, it is possible to observe stereoscopically even wider range in a direction along the optical axis.

A technical significance of conditional expression (2) is same as the technical significance of conditional expression (1). In a near-point observation, it is possible to realize a stereoscopic structure of a tissue of a gland duct, a capillary blood vessel, and the like, without fatigue. Moreover, in a far-point observation, since the inward angle becomes 3 degrees or more than 3 degrees, it is possible to realize a stereoscopic structure of the overall tissue.

It is preferable that the following conditional expression (2') be satisfied instead of conditional expression (2).

$$0.025 \leq ((-L/2) \times (f1/f2)) \times (1/WD') \leq 0.2 \quad (2')$$

It is more preferable that the following conditional expression (2") be satisfied instead of conditional expression (2).

$$0.025 \leq ((-L/2) \times (f1/f2)) \times (1/WD') \leq 0.1 \quad (2'')$$

In the stereoscopic vision optical system according to the second embodiment, it is preferable that the rear-side lens group include the movable lens, and the movable lens is a lens positioned nearest to the object in the first rear group and a lens positioned nearest to the object in the second rear group.

It is preferable that the movable lens have a large refractive power and be small-sized. By the refractive power being large, it is possible to make an amount of movement small. Moreover, being small-sized, it is possible to move and stop the lens in a short time.

When the refractive power of the movable lens is small, the amount of movement becomes large. When the refractive power of the movable lens is made large, it is possible to make the amount of movement small, but the number of lenses for improving an optical performance increases. Consequently, a thickness in an optical axial direction becomes large. In this case, since a member to be moved becomes large, the member becomes heavy. For moving the heavy member largely, it becomes necessary to make strength of a moving mechanism large and to increase an amount of a moving force. As a result, the moving mechanism becomes large in size.

A diameter of both the lens positioned nearest to the object in the first rear group and the lens positioned nearest to the object in the second rear group is small. Therefore, even when the refractive power is made large in these lenses, it is possible to suppress an increase in the number of lenses and to suppress the lenses from becoming large in size. Moreover, since it is possible to suppress the lenses from becoming large in size, it is possible to make these lenses lightweight.

For such reasons, in the stereoscopic vision optical system according to the second embodiment, the lens positioned nearest to the object in the first rear group and the lens positioned nearest to the object in the second rear group are used for the movable lenses. In this case, since it is possible to make the moving mechanism small-sized, it is possible to carry out focusing at a high speed.

In the stereoscopic vision optical system according to the second embodiment, it is preferable that the second lens group include the movable lens.

In a case in which the rear-side lens group includes the movable lens, movement of a lens is carried out in two optical paths. In other words, the movement of a lens is carried out in an optical path of the first rear group and an optical path of the second rear group. Whereas, in a case in which the second lens group includes the movable lens, the movement of a lens is carried out in one optical path. Therefore, it is possible to simplify the moving mechanism.

In a case in which the movement of a lens is carried out in the two optical paths, since the two lenses have to be moved simultaneously and equally, the adjustment becomes difficult. Whereas, in a case in which the second lens group includes the movable lens, the adjustment becomes easy.

In the stereoscopic vision optical system according to the second embodiment, it is preferable that the following conditional expression (3) be satisfied:

$$-0.001 \leq 1/f12w \leq 0.01 \quad (3)$$

where, f12w denotes a combined focal length of the first lens group and the second lens group at the time of a far-point observation, and the far-point observation is an observation in a state of being focused to the object at the far point.

In a case of falling below a lower limit value of conditional expression (3), a lens diameter of the rear-side lens group becomes large. Consequently, small-sizing of the optical system becomes difficult. In a case of exceeding an upper limit value of conditional expression (3), a light ray height at the lens positioned nearest to the object in the first lens group (hereinafter, referred to as 'front-end lens') becomes high. In this case, since a diameter of the front-end lens becomes large, small-sizing of the optical system becomes difficult.

An optical system formed by the first lens group and the second lens group may be made an afocal optical system. When such an arrangement is made, it is possible to make an outer diameter of lenses large.

At the time of proximity observation, a light ray with a wide angle of view is incident on the front-end lens. When the optical system formed by the first lens group and the second lens group is an afocal optical system, even in a case of carrying out focusing by the second lens group at the time of proximity observation, since the height of a light ray incident on the front-end lens becomes low, it is possible to make an outer diameter of the front-end lens small.

An endoscope according to the present embodiment includes the stereoscopic vision optical system according to the present embodiment, and an image sensor which captures an optical image formed by the stereoscopic vision optical system.

According to the endoscope of the present embodiment, it is possible to observe a sharp stereoscopic image with an appropriate stereoscopic effect at the time of the near-point observation.

Example of the stereoscopic vision optical system will be described below in detail by referring to the accompanying diagrams. However, the present disclosure is not restricted to the examples described below.

Lens cross-sectional views of each example will be described below. FIG. 1 is a lens cross-sectional view of an optical system in which an object position to be focused is fixed. Moreover, lens cross-sectional views other than FIG. 1 are lens cross-sectional views of optical systems in which the object position to be focused is variable.

FIG. 3A, FIG. 5A, FIG. 7A, and FIG. 9A are lens cross-sectional views at the time of focusing to a far point (far-point observation). FIG. 3B, FIG. 5B, FIG. 7B, and FIG. 9B are lens cross-sectional views at the time of focusing to a near point (near-point observation).

A first lens group is denoted by G1, a second lens group is denoted by G2, a third lens group is denoted by G3, an aperture stop is denoted by S, and an image plane (image pickup surface) is denoted by I. Moreover, a cover glass C1 and a cover glass C2 are disposed between the third lens group G3 and the image plane I.

The third lens group G3 is the rear-side lens group. The third lens group G3 includes a first rear group and a second rear group. An optical system which is identical to the first rear group is used for the second rear group. In the lens cross-sectional views of examples 3 to 5, only the first rear group is shown.

Aberration diagrams of each example will be described below. FIG. 2A shows a transverse aberration (DZY), FIG. 2B shows an astigmatism (AS), and FIG. 2C shows a distortion (DT). All the aberration diagrams are aberration diagrams at the object best position.

FIG. 4A, FIG. 6A, FIG. 8A, and FIG. 10A show a transverse aberration (DZY) at the time of focusing to a far point. FIG. 4B, FIG. 6B, FIG. 8B, and FIG. 10B show an astigmatism (AS) at the time of focusing to a far point. FIG. 4C, FIG. 6C, FIG. 8C, and FIG. 10C show a distortion (DT) at the time of focusing to a far point.

FIG. 4D, FIG. 6D, FIG. 8D, and FIG. 10D show a transverse aberration (DZY) at the time of focusing to a near point. FIG. 4E, FIG. 6E, FIG. 8E, and FIG. 10E show an astigmatism (AS) at the time of focusing to a near point. FIG. 4F, FIG. 6F, FIG. 8F, and FIG. 10F show a distortion (DT) at the time of focusing to a near point.

In each aberration diagram, a horizontal axis indicates an aberration amount. For the transverse aberration and the astigmatism, the unit of aberration amount is mm. Moreover, for the distortion, the unit of aberration amount is %. The unit of a wavelength of an aberration curve is nm.

A stereoscopic vision optical system of an example 1 includes in order from an object side, a first lens group G1 having a negative refractive power, a second lens group G2 having a positive refractive power, and a third lens group G3 having a positive refractive power. An aperture stop (A stop) S is disposed between the second lens group G2 and the third lens group G3.

The first lens group G1 includes a planoconcave negative lens L1 having a flat surface directed toward the object side and a biconcave negative lens L2.

The second lens group G2 includes a positive meniscus lens L3 having a convex surface directed toward the object side, a biconcave negative lens L4, a biconvex positive lens L5, and a planoconvex positive lens L6 having a flat surface directed toward an image side. Here, the biconcave negative lens L4 and the biconvex positive lens L5 are cemented.

The third lens group G3 includes a first rear group and a second rear group. Both the first rear group and the second rear group include a negative meniscus lens L7 having a convex surface directed toward the image side, a biconcave negative lens L8, a biconvex positive lens L9, a negative meniscus lens L10 having a convex surface directed toward the object side, a biconvex positive lens L11, a positive meniscus lens L12 having a convex surface directed toward the object side, and a negative meniscus lens L13 having a convex surface directed toward the object side.

Here, the biconcave negative lens L8 and the biconvex positive lens L9 are cemented. The negative meniscus lens L10 and the biconvex positive lens L11 are cemented. The positive meniscus lens L12 and the negative meniscus lens L13 are cemented.

The stereoscopic vision optical system of the example 1 is not provided with a focusing function. Therefore, all the lenses are fixed all the time.

A stereoscopic vision optical system of an example 2 includes in order from an object side, a first lens group G1 having a negative refractive power, a second lens group G2 having a positive refractive power, and a third lens group G3 having a positive refractive power. An aperture stop (A stop) S is disposed between the second lens group G2 and the third lens group G3.

The first lens group G1 includes a planoconcave negative lens L1 having a flat surface directed toward the object side and a biconcave negative lens L2.

The second lens group G2 includes a positive meniscus lens L3 having a convex surface directed toward the object side, a biconcave negative lens L4, a biconvex positive lens L5, and a planoconvex positive lens L6 having a flat surface directed toward an image side. Here, the biconcave negative lens L4 and the biconvex positive lens L5 are cemented.

The third lens group G3 includes a first rear group and a second rear group. Both the first rear group and the second rear group include a negative meniscus lens L7 having a convex surface directed toward the image side, a biconcave negative lens L8, a biconvex positive lens L9, a negative meniscus lens L10 having a convex surface directed toward the object side, a biconvex positive lens L11, a positive meniscus lens L12 having a convex surface directed toward the object side, and a negative meniscus lens L13 having a convex surface directed toward the object side.

Here, the biconcave negative lens L8 and the biconvex positive lens L9 are cemented. The negative meniscus lens L10 and the biconvex positive lens L11 are cemented. The positive meniscus lens L12 and the negative meniscus lens L13 are cemented.

The stereoscopic vision optical system of the example 2 is provided with a focusing function. The movable lenses are, the positive meniscus lens L3, the biconcave negative lens L4, the biconvex positive lens L5, and the planoconvex positive lens L6. At the time of focusing from a far point to a near point, the entire second lens group G2 moves toward the image side.

In the stereoscopic vision optical system of the example 2, the entire one lens group being moved, it is possible to simplify the moving mechanism.

In the stereoscopic vision optical system of the example 2, a combined optical system formed by the first lens group and the second lens group is an afocal optical system.

A stereoscopic vision optical system of an example 3 includes in order from an object side, a first lens group G1 having a negative refractive power, a second lens group G2 having a positive refractive power, and a third lens group G3 having a positive refractive power. An aperture stop (A stop) S is disposed between the second lens group G2 and the third lens group G3.

The first lens group G1 includes a planoconcave negative lens L1 having a flat surface directed toward the object side and a biconcave negative lens L2.

The second lens group G2 includes a positive meniscus lens L3 having a convex surface directed toward the object side, a biconcave negative lens L4, a biconvex positive lens L5, and a planoconvex positive lens L6 having a flat surface directed toward an image side. Here, the biconcave negative lens L4 and the biconvex positive lens L5 are cemented.

The third lens group G3 includes a first rear group and a second rear group. Both the first rear group and the second rear group include a negative meniscus lens L7 having a convex surface directed toward the image side, a biconcave negative lens L8, a biconvex positive lens L9, a negative meniscus lens L10 having a convex surface directed toward the object side, a biconvex positive lens L11, a positive meniscus lens L12 having a convex surface directed toward the object side, and a negative meniscus lens L13 having a convex surface directed toward the object side.

Here, the biconcave negative lens L8 and the biconvex positive lens L9 are cemented. The negative meniscus lens L10 and the biconvex positive lens L11 are cemented. The positive meniscus lens L12 and the negative meniscus lens L13 are cemented.

The stereoscopic vision optical system of the example 3 is provided with a focusing function. The negative meniscus lens L7 in the third lens group G3 is the movable lens. At the time of focusing from a far point to a near point, the negative meniscus lens L7 moves toward the object side.

In the stereoscopic vision optical system of the example 3, a combined optical system formed by the first lens group and the second lens group is an afocal optical system.

A stereoscopic vision optical system of an example 4 includes in order from an object side, a first lens group G1 having a negative refractive power, a second lens group G2 having a positive refractive power, and a third lens group G3 having a positive refractive power. An aperture stop (A stop) S is disposed between the second lens group G2 and the third lens group G3.

The first lens group G1 includes a planoconcave negative lens L1 having a flat surface directed toward the object side, a biconcave negative lens L2, and a biconvex positive lens L3. Here, the biconcave negative lens L2 and the biconvex positive lens L3 are cemented.

The second lens group G2 includes a biconcave negative lens L4, a biconvex positive lens L5, and a planoconvex positive lens L6 having a flat surface directed toward an image side. Here, the biconcave negative lens L4 and the biconvex positive lens L5 are cemented.

The third lens group G3 includes a first rear group and a second rear group. Both the first rear group and the second rear group include a negative meniscus lens L7 having a convex surface directed toward the image side, a biconcave negative lens L8, a biconvex positive lens L9, a negative meniscus lens L10 having a convex surface directed toward the object side, a biconvex positive lens L11, a biconvex positive lens L12, and a biconcave negative lens L13.

Here, the biconcave negative lens L8 and the biconvex positive lens L9 are cemented. The negative meniscus lens L10 and the biconvex positive lens L11 are cemented. The biconvex positive lens L12 and the biconcave negative lens L13 are cemented.

The stereoscopic vision optical system of the example 4 is provided with a focusing function. The negative meniscus lens L7 in the third lens group G3 is the movable lens. At the time of focusing from a far point to a near point, the negative meniscus lens L7 moves toward the object side.

In the stereoscopic vision optical system of the example 4, a diameter of the movable lens being small, a volume of the movable lens is small. In this case, since it is possible to make small a lens frame holding the movable lens, it is possible to make the optical system and the moving mechanism small-sized. Moreover, the movable lens being lightweight, it is possible to carry out focusing at a high speed.

In the stereoscopic vision optical system of the example 4, a combined optical system formed by the first lens group and the second lens group is an afocal optical system.

A stereoscopic vision optical system of an example 5 includes in order from an object side, a first lens group G1 having a negative refractive power, a second lens group G2 having a positive refractive power, and a third lens group G3 having a positive refractive power. An aperture stop (A stop) is disposed between the second lens group G2 and the third lens group G3.

The first lens group G1 includes a planoconcave negative lens L1 having a flat surface directed toward the object side and a biconcave negative lens L2.

The second lens group G2 includes a biconcave negative lens L3, a biconvex positive lens L4, and a planoconvex positive lens L5 having a flat surface directed toward an image side. Here, the biconcave negative lens L3 and the biconvex positive lens L4 are cemented.

The third lens group G3 includes a first rear group and a second rear group. Both the first rear group and the second rear group include a negative meniscus lens L6 having a convex surface directed toward the image side, a negative meniscus lens L7 having a convex surface directed toward the object side, a biconvex positive lens L8, a biconvex positive lens L9, a negative meniscus lens L10 having a convex surface directed toward the image side, a biconvex positive lens L11, and a biconcave negative lens L12.

Here, the negative meniscus lens L7 and the biconvex positive lens L8 are cemented. The biconvex positive lens L9 and the negative meniscus lens L10 are cemented. The biconvex positive lens L11 and the biconcave negative lens L12 are cemented.

The stereoscopic vision optical system of the example 5 is provided with a focusing function. The negative meniscus lens L6 in the third lens group G3 is the movable lens. At the time of focusing from a far point to a near point, the negative meniscus lens L6 moves toward the object side.

In the stereoscopic vision optical system of the example 5, a diameter of the movable lens being small, a volume of the movable lens is small. In this case, since it is possible to make small a lens frame holding the movable lens, it is possible to make the optical system and the moving mechanism small-sized. Moreover, the movable lens being lightweight, it is possible to carry out focusing at a high speed.

In the stereoscopic vision optical system of the example 5, a combined optical system formed by the first lens group and the second lens group is an afocal optical system. In a combined optical system, an afocal magnification being 0.55 times which is high, it is possible to make large the inward angle at the time of the near-point observation.

Numerical data of each example described above is shown below. In surface data, r denotes radius of curvature of each lens surface, d denotes a distance between respective lens surfaces, nd denotes a refractive index of each lens for a d-line, vd denotes an Abbe number for each lens.

In various data, IH denotes an image height, $\phi$ denotes an aperture stop diameter, L denotes a distance between an optical axis of the first rear group and an optical axis of the second rear group, NA denotes a numerical aperture on the object side, and $\Delta I$ denotes an amount of shift of the image plane. FObs denotes at the time of the far-point observation and Nobs denotes at the time of the near-point observation.

An amount of shift of the third lens group is to be calculated from a distance between an optical axis of the first lens group and the optical axis of the first rear group, or from a distance between the optical axis of the first lens group and the optical axis of the second rear group.

A first optical image is formed on an image plane of the first rear group. A second optical image is formed on an image plane of the second rear group. Both a position of the optical axis of the first rear group and a position of the optical axis of the second rear group are shifted with respect to the optical axis of the first lens group. Consequently, an image of an object point on the optical axis of the first lens group is not formed on the optical axis of the first rear group and the optical axis of the second rear group. In other words, a center of the first optical image does not coincide with the optical axis of the first rear group, and a center of the second optical image does not coincide with the optical axis of the second rear group.

The amount of shift of the image plane is to be calculated from a difference in the optical axis of the first rear group and the center of the first optical image, or, from a difference in the optical axis of the second rear group and the center of the second optical image. Regarding the plus or minus sign of a reference numeral for the shift amount of the image plane, in a case in which the center of the first optical image is on the optical axis side of the first lens group than the optical axis of the first rear group, and in a case in which the center of the second optical image is on the optical axis side of the first lens group than the optical axis of the second rear group, the sign is minus.

Example 1

| | Unit mm Surface data | | | |
|---|---|---|---|---|
| Surface no. | r | d | nd | vd |
| Object plane | ∞ | 2.0000 | | |
| 1 | ∞ | 0.2800 | 1.88300 | 40.76 |
| 2 | 1.3245 | 0.5700 | | |
| 3 | −10.8074 | 0.2500 | 1.72916 | 54.68 |
| 4 | 7.6830 | 0.3568 | | |
| 5 | 3.3770 | 0.5300 | 1.76182 | 26.52 |
| 6 | 6.0187 | 0.1558 | | |
| 7 | −7.4569 | 0.3100 | 1.85026 | 32.27 |
| 8 | 8.3598 | 0.6900 | 1.58913 | 61.14 |
| 9 | −1.9473 | 0.0500 | | |
| 10 | 6.9935 | 0.3500 | 1.81600 | 46.62 |
| 11 | ∞ | 0.0000 | | |
| 12 (Stop) | ∞ | 0.05802 | | |
| 13 | −0.5469 | 0.2976 | 1.72916 | 54.68 |
| 14 | −1.0415 | 0.0759 | | |
| 15 | −7.3521 | 0.1740 | 1.80518 | 25.42 |
| 16 | 1.0078 | 0.5184 | 1.74100 | 52.64 |
| 17 | −1.2793 | 0.0435 | | |
| 18 | 3.0136 | 0.1920 | 1.81600 | 46.62 |
| 19 | 2.3399 | 0.4608 | 1.84666 | 23.78 |
| 20 | −6.6867 | 0.0725 | | |
| 21 | 1.2174 | 0.6240 | 1.81600 | 46.62 |
| 22 | 13.3260 | 0.2031 | 1.92286 | 18.90 |
| 23 | 0.6192 | 0.2901 | | |
| 24 | ∞ | 0.2719 | 1.51633 | 64.14 |
| 25 | ∞ | 0.0109 | 1.51000 | 64.05 |
| 26 | ∞ | 0.2176 | 1.50510 | 63.26 |
| 27 | ∞ | 0.0000 | | |
| Image plane | ∞ | | | |

| Various data | |
|---|---|
| IH | 0.48 |
| $\phi$ | 0.32 |
| L | 1.4 |
| NA | 0.0194 |
| $\Delta I$ | 0.0119 |

Example 2

Unit mm
Surface data

| Surface no. | r | d | nd | νd |
|---|---|---|---|---|
| Object plane | ∞ | d0 | | |
| 1 | ∞ | 0.2800 | 1.88300 | 40.76 |
| 2 | 1.3245 | 0.5700 | | |
| 3 | −10.8074 | 0.2500 | 1.72916 | 54.68 |
| 4 | 7.6830 | d1 | | |
| 5 | 3.3770 | 0.5300 | 1.76182 | 26.52 |
| 6 | 6.0187 | 0.1558 | | |
| 7 | −7.4569 | 0.3100 | 1.85026 | 32.27 |
| 8 | 8.3598 | 0.6900 | 1.58913 | 61.14 |
| 9 | −1.9473 | 0.0500 | | |
| 10 | 6.9935 | 0.3500 | 1.81600 | 46.62 |
| 11 | ∞ | 0.0000 | | |
| 12 (Stop) | ∞ | d2 | | |
| 13 | −0.5469 | 0.2976 | 1.72916 | 54.68 |
| 14 | −1.0415 | 0.0759 | | |
| 15 | −7.3521 | 0.1740 | 1.80518 | 25.42 |
| 16 | 1.0078 | 0.5184 | 1.74100 | 52.64 |
| 17 | −1.2793 | 0.0435 | | |
| 18 | 3.0136 | 0.1920 | 1.81600 | 46.62 |
| 19 | 2.3399 | 0.4608 | 1.84666 | 23.78 |
| 20 | −6.6867 | 0.0725 | | |
| 21 | 1.2174 | 0.6240 | 1.81600 | 46.62 |
| 22 | 13.3260 | 0.2031 | 1.92286 | 18.90 |
| 23 | 0.6192 | 0.2901 | | |
| 24 | ∞ | 0.2719 | 1.51633 | 64.14 |
| 25 | ∞ | 0.0109 | 1.51000 | 64.05 |
| 26 | ∞ | 0.2176 | 1.50510 | 63.26 |
| 27 | ∞ | 0.0000 | | |
| Image plane | ∞ | | | |

Various data

| | FObs | NObs |
|---|---|---|
| IH | 0.48 | |
| φ | 0.32 | |
| L | 1.4 | |
| NA | 0.0058 | 0.0194 |
| ΔI | 0.0171 | 0.0119 |
| d0 | 10 | 2 |
| d1 | 0.1 | 0.3568 |
| d2 | 0.3148 | 0.05802 |

Example 3

Unit mm
Surface data

| Surface no. | r | d | nd | νd |
|---|---|---|---|---|
| Object plane | ∞ | d0 | | |
| 1 | ∞ | 0.2800 | 1.88300 | 40.76 |
| 2 | 1.3245 | 0.5700 | | |
| 3 | −10.8074 | 0.2500 | 1.72916 | 54.68 |
| 4 | 7.6830 | 0.1000 | | |
| 5 | 3.3770 | 0.5300 | 1.76182 | 26.52 |
| 6 | 6.0187 | 0.1558 | | |
| 7 | −7.4569 | 0.3100 | 1.85026 | 32.27 |
| 8 | 8.3598 | 0.6900 | 1.58913 | 61.14 |
| 9 | −1.9473 | 0.0500 | | |
| 10 | 6.9935 | 0.3500 | 1.81600 | 46.62 |
| 11 | ∞ | 0.0000 | | |
| 12 (Stop) | ∞ | d1 | | |
| 13 | −0.5469 | 0.2976 | 1.72916 | 54.68 |
| 14 | −1.0415 | d2 | | |
| 15 | −7.3521 | 0.1740 | 1.80518 | 25.42 |
| 16 | 1.0078 | 0.5184 | 1.74100 | 52.64 |
| 17 | −1.2793 | 0.0435 | | |
| 18 | 3.0136 | 0.1920 | 1.81600 | 46.62 |
| 19 | 2.3399 | 0.4608 | 1.84666 | 23.78 |
| 20 | −6.6867 | 0.0725 | | |
| 21 | 1.2174 | 0.6240 | 1.81600 | 46.62 |
| 22 | 13.3260 | 0.2031 | 1.92286 | 18.90 |
| 23 | 0.6192 | 0.2901 | | |
| 24 | ∞ | 0.2719 | 1.51633 | 64.14 |
| 25 | ∞ | 0.0109 | 1.51000 | 64.05 |
| 26 | ∞ | 0.2176 | 1.50510 | 63.26 |
| 27 | ∞ | 0.0000 | | |
| Image plane | ∞ | | | |

Various data

| | FObs | NObs |
|---|---|---|
| IH | 0.48 | |
| φ | 0.32 | |
| L | 1.4 | |
| NA | 0.0058 | 0.021 |
| ΔI | 0.0171 | 0.0441 |
| d0 | 10 | 2 |
| d1 | 0.3148 | 0.1605 |
| d2 | 0.0759 | 0.2304 |

Example 4

Unit mm
Surface data

| Surface no. | r | d | nd | νd |
|---|---|---|---|---|
| Object plane | ∞ | d0 | | |
| 1 | ∞ | 0.2800 | 1.88300 | 40.76 |
| 2 | 1.5954 | 0.7800 | | |
| 3 | −2.8360 | 0.2500 | 1.72916 | 54.68 |
| 4 | 3.1630 | 0.5600 | 1.76182 | 26.52 |
| 5 | −4.0801 | 0.2748 | | |
| 6 | −22.4094 | 0.3100 | 1.85026 | 32.27 |
| 7 | 2.5977 | 0.6900 | 1.58913 | 61.14 |
| 8 | −2.6295 | 0.0500 | | |
| 9 | 6.9935 | 0.3500 | 1.81600 | 46.62 |
| 10 | ∞ | 0.0000 | | |
| 11 (Stop) | ∞ | d1 | | |
| 12 | −0.6134 | 0.1983 | 1.72916 | 54.68 |
| 13 | −1.0303 | d2 | | |
| 14 | −32.2876 | 0.1813 | 1.84666 | 23.78 |
| 15 | 3.7133 | 0.6345 | 1.74100 | 52.64 |
| 16 | −1.3349 | 0.0453 | | |
| 17 | 4.7228 | 0.2115 | 1.81600 | 46.62 |
| 18 | 1.1500 | 0.6043 | 1.80100 | 34.97 |
| 19 | −7.5918 | 0.0755 | | |
| 20 | 1.8280 | 0.7101 | 1.72916 | 54.68 |
| 21 | −1.4581 | 0.2115 | 1.92286 | 18.90 |
| 22 | 2.8612 | 0.3022 | | |
| 23 | ∞ | 0.2833 | 1.51633 | 64.14 |
| 24 | ∞ | 0.0113 | 1.51000 | 64.05 |
| 25 | ∞ | 0.2266 | 1.50510 | 63.26 |
| 26 | ∞ | 0.0000 | | |
| Image plane | ∞ | | | |

Various data

| | FObs | NObs |
|---|---|---|
| IH | 0.48 | |
| φ | 0.344 | |
| L | 1.4 | |
| NA | 0.0061 | 0.0217 |
| ΔI | 0.0212 | 0.0463 |
| d0 | 10 | 2 |
| d1 | 0.5385 | 0.3225 |
| d2 | 0.0847 | 0.2803 |

Example 5

| | | Unit mm Surface data | | |
|---|---|---|---|---|
| Surface no. | r | d | nd | vd |
| Object plane | ∞ | d0 | | |
| 1 | ∞ | 0.2800 | 1.88300 | 40.76 |
| 2 | 1.6970 | 0.5300 | | |
| 3 | −6.3656 | 0.2400 | 1.95906 | 17.47 |
| 4 | 6.9557 | 0.1220 | | |
| 5 | −134.6132 | 0.2000 | 1.80518 | 25.42 |
| 6 | 4.7777 | 0.5500 | 2.00330 | 28.27 |
| 7 | −2.6535 | 0.0500 | | |
| 8 | 9.1945 | 0.2500 | 1.81600 | 46.62 |
| 9 | ∞ | 0.0000 | | |
| 10 (Stop) | ∞ | d1 | | |
| 11 | −0.4413 | 0.1189 | 1.56873 | 63.10 |
| 12 | −0.8733 | d2 | | |
| 13 | 4.1891 | 0.1358 | 1.84666 | 23.78 |
| 14 | 0.8015 | 0.4075 | 1.78800 | 47.37 |
| 15 | −1.1624 | 0.0272 | | |
| 16 | 1.8918 | 0.2264 | 1.80610 | 40.92 |
| 17 | −0.8160 | 0.2717 | 1.81600 | 46.62 |
| 18 | −55.0403 | 0.0453 | | |
| 19 | 1.1662 | 0.4415 | 1.74100 | 52.64 |
| 20 | −0.8520 | 0.1189 | 1.78472 | 25.68 |
| 21 | 1.1256 | 0.1811 | | |
| 22 | ∞ | 0.1698 | 1.51633 | 64.14 |
| 23 | ∞ | 0.0068 | 1.51000 | 64.05 |
| 24 | ∞ | 0.1358 | 1.50510 | 63.26 |
| 25 | ∞ | 0.0000 | | |
| Image plane | ∞ | | | |

| Various data | | |
|---|---|---|
| IH | 0.42 | |
| φ | 0.432 | |
| L | 1.4 | |
| | FObs | NObs |
| N | 0.0061 | 0.2607 |
| ΔI | 0.026 | 0.0588 |
| d0 | 10 | 2 |
| d1 | 0.3099 | 0.1163 |
| d2 | 0.0671 | 0.2607 |

Next, values of conditional expressions in each example are given below. '-' (hyphen) indicates that there is no corresponding arrangement.

| | Example1 | Example2 | Example3 |
|---|---|---|---|
| (1) ((−L/2) × (f1/f2)) × (1/WD) | 0.14 | 0.14 | 0.14 |
| (2) ((−L/2) × (f1/f2)) × (1/WD') | — | 0.028 | 0.028 |
| (3) 1/f12w | 1.61E-9 | 1.61E-9 | 1.61E-9 |

| | Example4 | Example5 |
|---|---|---|
| (1) ((−L/2) × (f1/f2)) × (1/WD) | 0.14 | 0.198 |
| (2) ((−L/2) × (f1/f2)) × (1/WD') | 0.028 | 0.039 |
| (3) 1/f12w | −5.92E-9 | 4.22E-9 |

Figure 11:
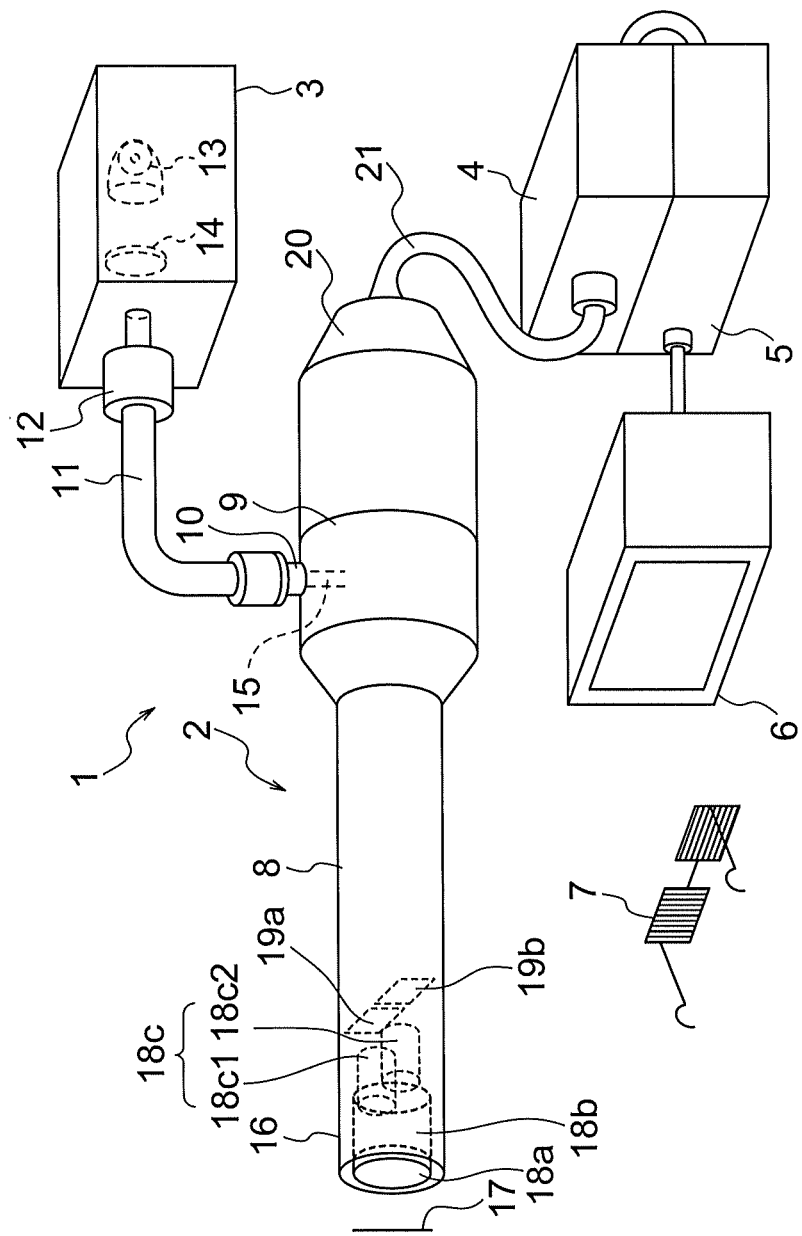
FIG. 11 is a diagram showing an endoscope of the present embodiment.

FIG. 11 is a diagram showing an endoscope of the present embodiment. The endoscope of the present embodiment is a stereoscopic-vision endoscope. A stereoscopic-vision endoscope 1 includes a body portion 2, a light-source unit 3, a camera control unit 4 (hereinafter, referred to as 'CCU 4'), a scan converter 5, a monitor 6, and shutter glasses 7.

The body portion 2 includes an insertion portion 8 and a holding portion 9. The insertion portion 8 is a portion to be inserted into a body cavity, and is formed by a hard jacket tube. The jacket tube is in the form of a circular tube, and is made of a metal such as stainless steel. In such manner, the stereoscopic-vision endoscope 1 is a rigid endoscope. The holding portion 9 is a portion to be held by an operator.

The holding portion 9 is provided with a light-guide tube 10. One end of a light-guide cable 11 is connected to the light-guide tube 10. The other end of the light-guide cable 11 is provided with alight-guide connector 12. The light-guide cable 11 is detachably connected to the holding portion 9 and the light-source unit 3.

The light-source unit 3 includes a lamp 13 and a lens 14. The lamp 13 generates illumination light such as white light. The lens 14 focuses the illumination light. The illumination light focused by the lens 14 is irradiated to an end surface of the light-guide connector 12. The illumination light irradiated to the end surface is transmitted to the body portion 2 by a light guide inside the light-guide cable 11.

The body portion 2 is provided with a light guide 15. The light guide 15 is bent inside the holding portion 9, and is passed through the insertion portion 8. The light guide 15 transmits the illumination light supplied from the light-guide cable 11 to a front-end surface which is fixed to a front-end portion 16 of the insertion portion 8. Accordingly, the illumination light is emerged frontward from the front-end surface.

Inside of the front-end portion 16, a stereoscopic vision optical system of the present embodiment is disposed. The stereoscopic vision optical system includes a first lens group 18a, a second lens group 18b, and a rear-side lens group 18c. The rear-side lens group 18c includes a first rear group 18c1 and a second rear group 18c2.

An object 17 is illuminated by the illumination light. Light from the object 17 is incident on the first lens group 18a and the second lens group 18b. Light emerged from the second lens group 18b is incident on the first rear group 18c1, and thereby a first optical image is formed at an image forming position. Light emerged from the second lens group 18b is incident on the second rear group 18c2, and thereby a second optical image is formed at an image forming position.

The first optical image and the second optical image are formed same region. Therefore, when the first optical image and the second optical image are captured, one image sensor or two image sensor may be used. In the stereoscopic-vision endoscope 1, an image sensor 19a and an image sensor 19b are disposed on the image forming position.

One end of a signal cable 21 is connected to an output portion 20. The other end of the signal cable 21 is connected to the CCU 4. A signal which is output from the image sensor 19a and the image sensor 19b are input to the CCU 4 via the signal cable 21.

In the CCU 4, signal processing is carried out on signals output from the image sensor 19 a and the image sensor 19b. An image signal subjected to signal processing in the CCU 4 is input to the scan converter 5. In the scan converter 5, the signal output from the CCU 4 is converted to a video signal.

The video signal is input to the monitor 6. The monitor 6 displays the video signal that has been input. Two images having a parallax are displayed alternately on the monitor 6.

The shutter glasses 7 have a shutter function. By using the shutter glasses 7, images displayed on the monitor 6 can be viewed stereoscopically.

According to the present disclosure, it is possible to provide a stereoscopic vision optical system in which an appropriate stereoscopic effect can be achieved and aberrations are corrected favorably, while being small-sized, and an endoscope using the stereoscopic vision optical system.

As described heretofore, the present disclosure is suitable for a stereoscopic vision optical system in which an appropriate stereoscopic effect can be achieved and aberrations are corrected favorably, while being small-sized, and an endoscope using the stereoscopic vision optical system.

What is claimed is:

1. A stereoscopic vision optical system, comprising in order from an object side to an image side:
a first lens group having a negative refractive power, the first lens group being disposed nearest to an object;
a second lens group having a positive refractive power, and
a rear-side lens group having a positive refractive power, wherein:
the rear-side lens group includes a first rear group and a second rear group,
the first lens group and the second lens group are aligned in a straight line,
an optical axis of the first lens group and an optical axis of the second lens group coincide with the straight line,
the optical axis of the first lens group, an optical axis of the first rear group, and an optical axis of the second rear group are positioned on a same plane,
the optical axis of the first lens group is positioned between the optical axis of the first rear group and the optical axis of the second rear group, and
the following conditional expression (1) is satisfied:

$$0.08 \leq ((-L/2) \times (f1/f2)) \times (1/WD) \leq 0.25 \quad (1)$$

where:
L denotes a distance between the optical axis of the first rear group and the optical axis of the second rear group,
WD denotes a distance between an object best position and a surface nearest to the object of the first lens group,
f1 denotes a focal length of the first lens group,
f2 denotes a focal length of the second lens group, and
the object best position is an object position conjugate with the most focused position on an image plane.

2. A stereoscopic vision optical system, comprising in order from an object side to an image side:
a first lens group having a negative refractive power, the first lens group being disposed nearest to an object;
a second lens group having a positive refractive power, and
a rear-side lens group having a positive refractive power, wherein:
the rear-side lens group includes a first rear group and a second rear group,
the first lens group and the second lens group are aligned in a straight line,
an optical axis of the first lens group and an optical axis of the second lens group coincide with the straight line,
the optical axis of the first lens group, an optical axis of the first rear group, and an optical axis of the second rear group are positioned on a same plane,
the optical axis of the first lens group is positioned between the optical axis of the first rear group and the optical axis of the second rear group, one of the second lens group and the rear-side lens group includes a movable lens,
focusing is carried out by moving the movable lens parallel to the optical axis of the first lens group, and
both in a case of being focused to an object at a far point and in a case of being focused to an object at a near point, the following conditional expression (2) is satisfied:

$$0.025 \leq ((-L/2) \times (f1/f2)) \times (1/WD') \leq 0.25 \quad (2)$$

where:
L denotes a distance between the optical axis of the first rear group and the optical axis of the second rear group,
WD' denotes a distance between an object best position and a surface nearest to the object of the first lens group,
f1 denotes a focal length of the first lens group,
f2 denotes a focal length of the second lens group, and
the object best position is an object position conjugate with the most focused position on an image plane.

3. The stereoscopic vision optical system according to claim 2, wherein:
the rear-side lens group includes the movable lens, and
the movable lens is a lens positioned nearest to the object in the first rear group and a lens positioned nearest to the object in the second rear group.

4. The stereoscopic vision optical system according to claim 2, wherein the second lens group includes the movable lens.

5. The stereoscopic vision optical system according to claim 4, wherein the following conditional expression (3) is satisfied:

$$-0.001 \leq 1/f12w \leq 0.01 \quad (3)$$

where:
f12w denotes a combined focal length of the first lens group and the second lens group at a time of a far-point observation, and
the far-point observation is an observation in a state of being focused to the object at the far point.

6. An endoscope comprising:
a stereoscopic vision optical system according to claim 2; and
an image sensor which captures an optical image formed by the stereoscopic vision optical system.

7. The endoscope according to claim 6, wherein:
the rear-side lens group includes a movable lens, and
the movable lens is a lens positioned nearest to the object in the first rear group and a lens positioned nearest to the object in the second rear group.

8. The endoscope according to claim 6, wherein the second lens group includes a movable lens.

9. The endoscope according to claim 8, wherein the following conditional expression (3) is satisfied:

$$-0.001 \leq 1/f12w \leq 0.01 \quad (3)$$

where:
f12w denotes a combined focal length of the first lens group and the second lens group at the time of a far-point observation, and
the far point observation is an observation in a state of being focused to the object at the far point.

* * * * *